(12) United States Patent
Lee et al.

(10) Patent No.: US 12,114,982 B2
(45) Date of Patent: Oct. 15, 2024

(54) SKIN-MOUNTABLE ELECTRONIC DEVICES AND METHODS OF USING AND FABRICATING THE SAME

(71) Applicant: PURDUE RESEARCH FOUNDATION, West Lafayette, IN (US)

(72) Inventors: Chi Hwan Lee, West Lafayette, IN (US); Georgia Malandraki, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 517 days.

(21) Appl. No.: 15/876,977

(22) Filed: Jan. 22, 2018

(65) Prior Publication Data

US 2018/0271393 A1  Sep. 27, 2018

Related U.S. Application Data (60) Provisional application No. 62/595,345, filed on Dec. 6, 2017, provisional application No. 62/448,430, filed on Jan. 20, 2017.

(51) Int. Cl.
*A61B 5/01* (2006.01)
*A61B 5/00* (2006.01)
(Continued)

(52) U.S. Cl.
CPC ............. *A61B 5/282* (2021.01); *A61B 5/256* (2021.01); *A61B 5/296* (2021.01); *A61B 5/4205* (2013.01); *A61B 5/6833* (2013.01); *A61F 7/007* (2013.01); *A61M 37/00* (2013.01); *A61B 5/01* (2013.01); *A61B 5/14542* (2013.01); *A61B 5/4227* (2013.01); *A61B 2090/064* (2016.02); *A61B 2560/0412* (2013.01);
(Continued)

(58) Field of Classification Search
CPC ...... A61B 2090/064; A61B 2560/0412; A61B 2562/0209; A61B 2562/0261
See application file for complete search history.

(56) References Cited

U.S. PATENT DOCUMENTS

| | | | |
|---|---|---|---|
| 2013/0041235 A1* | 2/2013 | Rogers | A61B 5/1107 600/306 |
| 2015/0309535 A1* | 10/2015 | Connor | A61B 5/1477 361/679.03 |
| 2015/0335288 A1* | 11/2015 | Toth | A61B 5/6833 600/373 |

OTHER PUBLICATIONS

Jang, KI., Han, S., Xu, S et al. Rugged and breathable forms of stretchable electronics with adherent composite substrates for transcutaneous monitoring. Nat Commun 5, 4779 (2014). (Year: 2014).*
(Continued)

*Primary Examiner* — Tse W Chen
*Assistant Examiner* — Michael A Catina
(74) *Attorney, Agent, or Firm* — Hartman Global IP Law; Gary M. Hartman; Domenica N. S. Hartman (57) ABSTRACT

Skin-mountable electronic devices and methods suitable for fabricating and using the devices. One embodiment of such a device includes a flexible structure comprising a pattern of individual interconnected traces each comprising a portion of an electrically-conductive layer that overlies and directly contacts an underlying portion of an elastomeric layer. At least some of the portions of the electrically-conductive layer within the pattern are functional electrodes of the skin-mountable electronic device.

4 Claims, 10 Drawing Sheets

(51) Int. Cl.
    *A61B 5/256*     (2021.01)
    *A61B 5/282*     (2021.01)
    *A61B 5/296*     (2021.01)
    *A61F 7/00*     (2006.01)
    *A61M 37/00*     (2006.01)
    *A61B 5/145*     (2006.01)
    *A61B 90/00*     (2016.01)
    *A61M 35/00*     (2006.01)

(52) U.S. Cl.
    CPC ............... *A61B 2562/0209* (2013.01); *A61B 2562/0261* (2013.01); *A61B 2562/0285* (2013.01); *A61B 2562/125* (2013.01); *A61F 2007/0052* (2013.01); *A61F 2007/0071* (2013.01); *A61F 2007/0095* (2013.01); *A61M 35/00* (2013.01)

(56) References Cited

OTHER PUBLICATIONS

Personal Thermal Management by Metallic Nanowire-Coated Textile Po-Chun Hsu, Xiaoge Liu, Chong Liu, Xing Xie, Hye Ryoung Lee, Alex J. Welch, Tom Zhao, and Yi Cui Nano Letters 2015 15 (1), 365-371 (Year: 2015).*

* cited by examiner

SKIN-MOUNTABLE ELECTRONIC DEVICES AND METHODS OF USING AND FABRICATING THE SAME

CROSS REFERENCE TO RELATED APPLICATIONS

This application claims the benefit of U.S. Provisional Application Nos. 62/448,430 filed Jan. 20, 2017, and 62/595,345 filed Dec. 6, 2017. The contents of these prior applications are incorporated herein by reference.

BACKGROUND OF THE INVENTION

The present invention generally relates to electronic systems adapted to be temporarily attached to the skin of a user. The invention particularly relates to skin-mountable electronic devices and to methods for fabricating and using such devices.

Rapid development of mechanically non-conventional electronics has begun to open pathways to new products in the field of skin-mountable electronics that can intimately contact the skin while maintaining functionality and integration under repeated deformations, such as bending, stretching, compression, and twisting. Examples include sensors for monitoring temperature, pressure, oxygen concentration of blood, and electrophysiological activities, and actuators for delivering therapeutic heat and drugs. Coplanar thin films formed with ductile metals such as gold (Au), copper (Cu), silver (Ag), and platinum (Pt) have been employed to serve as conductive electrodes in skin-mountable electronic sensors, while precisely engineered stretchable layouts such as filamentary serpentines, self-similar fractals, and horseshoes have been employed as supporting elastomeric substrates and/or encapsulants to simultaneously allow efficient accommodation of mechanical deformations.

An ongoing challenge to the use of skin-mountable electronic devices includes the potential for catastrophic failures of such electrodes that may occur under unpredictable circumstances, such as inadvertent over-stretching beyond the fracture limits, defect-driven cracks, and edge-initiated delamination. Recent developments offer the possibility of alleviating such issues by exploiting microfluidic structures in which ultra-low modulus materials embedded inside a microfluidic space can thoroughly isolate the mechanics associated with the constituent thin film-based electrodes from the supporting elastomeric substrate/encapsulant. These strategies may potentially provide valuable means to endow the devices with necessary mechanical properties. However, current microfluidic structures undesirably increase the volume of skin-mountable electronic devices as a result of requiring additional layers to provide packaging for these structures.

In view of the above, it can be appreciated that there is an ongoing desire for skin-mountable electronic devices that exhibit mechanical properties capable of promoting the service lives of the devices.

BRIEF DESCRIPTION OF THE INVENTION

The present invention provides skin-mountable electronic devices and methods suitable for fabricating and using the devices.

According to one aspect of the invention, a skin-mountable electronic device includes a flexible structure comprising a pattern of individual interconnected traces each comprising a portion of an electrically-conductive layer that overlies and directly contacts an underlying portion of an elastomeric layer. At least some of the portions of the electrically-conductive layer within the pattern are functional electrodes of the skin-mountable electronic device.

Another aspect of the invention is a skin-mountable electronic device adapted for measuring muscle activity in a human body. The skin-mountable electronic device includes a flexible structure comprising a pattern of individual interconnected traces each comprising a portion of an electrically-conductive layer that overlies and directly contacts an underlying portion of an elastomeric layer. The device further includes functional electrodes located within the pattern and an electrical connector for electrically connecting an electronic unit to the functional electrodes. The electrical connector is electrically connected to at least some of the functional electrodes through different conductive paths defined by some of the portions of the electrically-conductive layer of the individual interconnected traces that are serially electrically connected to each other and are not electrically connected to other of the portions of the electrically-conductive layer of the individual interconnected traces.

Yet another aspect of the invention is a method of using a device comprising elements as described above. The method includes applying the skin-mountable electronic device to a surface of the skin of a human body so that the flexible structure is in direct physical contact with the skin, and then performing one of the following with the skin-mountable electronic device: monitoring a physiological parameter of the human body with the skin-mountable electronic device; or providing therapeutic heat or a therapeutic drug to the human body with the skin-mountable electronic device.

Still another aspect of the invention is a method of fabricating a skin-mountable electronic device. Such a method includes producing a stack comprising a substrate, an intermediate layer that overlies the substrate, an elastomeric layer that overlies the intermediate layer, and a nanowire mesh layer that overlies and directly contacts the elastomeric layer. The nanowire mesh layer and the elastomeric layer are then patterned and etched to define a pattern that overlies the intermediate layer. The pattern comprises individual interconnected traces each comprising a portion of the nanowire mesh layer that overlies and directly contacts an underlying portion of the elastomeric layer. The stack is then treated to promote debonding of the intermediate layer from the substrate, the pattern and the intermediate layer are simultaneously mechanically peeled from the substrate, and the intermediate layer is removed from the pattern to yield a nanocomposite elastomer structure that is a component of the skin-mountable electronic device in which portions of the nanowire mesh layer within the pattern are functional electrodes of the skin-mountable electronic device.

Technical effects of devices and methods of the types described above preferably include the ability to provide electronic devices suitable for use in a variety of diagnostic and/or treatment applications. Preferred aspects include the ability to fabricate such devices to exhibit enhanced mechanical properties that reduce the likelihood of fracture and/or delamination, and thereby extend the service lives of the devices.

Other aspects and advantages of this invention will be further appreciated from the following detailed description.

DETAILED DESCRIPTION OF THE INVENTION

Disclosed herein are skin-mountable electronic devices intended for use in systems capable of use in applications such as sensors for detecting physiological parameters of a living body as well as thermal actuators for delivering therapeutic heat or drugs to a living body. For example, such sensors may monitor temperature, pressure, oxygen concentration of blood, and/or electrophysiological activities of a wearer, and such thermal actuators may produce heat and optionally activate a thermally responsive polymer to release a pre-embedded drug that can then be absorbed through the skin of the wearer. The devices include a flexible structure comprising a pattern of individual interconnected traces each comprising an electrically-conductive layer that overlies and directly contacts an elastomeric layer. The electrically-conductive layer and its individual interconnected traces may be formed by a metallic thin film, in which case the flexible structure is referred to as a composite elastomer structure, or may be formed by an electrically-conductive nanowire (NW) mesh layer, in which case the flexible structure is referred to as a nanocomposite elastomer structure. Preferred nanowire mesh layers are made up of highly-networked systems of one-dimensional metallic nanowires, and at least some portions of the electrically-conductive nanowire mesh layer are adapted to serve as functional electrodes of the skin-mountable electronic device.

When used in ultra-thin, conformable electronic devices, preferred nanocomposite elastomer structures of this invention are capable of exhibiting enhanced mechanical properties that reduce the likelihood of fracture and delamination, and thereby potentially extend the service lifetime of the devices relative to composite elastomer structures comprising interconnected traces formed by metallic thin films. Investigations discussed below indicated that an electrically-conductive mesh layer of a highly-networked nanowires in combination with an elastomeric layer (serving as a substrate for the mesh layer) is capable of exhibiting superior crack resistance, contact adhesion, and normal/shear strength in comparison to metallic thin film-based counterparts. Device demonstrations in thermotherapeutic treatments of joints, surface temperature mapping of skin, and electrophysiological monitoring of the heart and muscles evidenced the potential for practical applications with importance for human healthcare.

According to a first nonlimiting embodiment, in a flexible nanocomposite elastomer structure containing an electrically-conductive mesh layer of highly-networked nanowires and an elastomeric layer, at least portions of the mesh layer serve as electrical conducting elements and the elastomeric layer serves an elastomeric substrate or matrix for the mesh layer. The nanowires may be formed of any metallic material, including but not limited to ductile metals such as gold (Au), copper (Cu), silver (Ag), and platinum (Pt). In the investigations below, Cu nanowires and Ag nanowires were studied due to their high electrical conductivity as well as excellent elongation properties. Nonlimiting examples of suitable materials for the elastomeric layer include biocompatible elastomeric polymers such as diluted polyimide (D-PI, 1:1 ratio mixture of polyimide and 1-Methyl-2-pyrrolidinone) and polydimethylsiloxane (PDMS).

Figure 1:
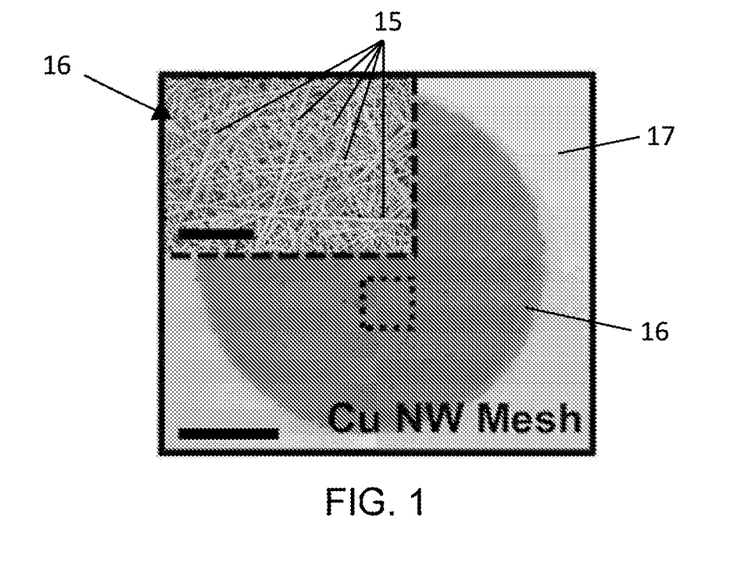
FIG. 1 contains optical images of a nanowire mesh layer of a type suitable for use in skin-mountable electronic devices in accordance with nonlimiting embodiments of the present invention.

FIG. 1 shows optical images of an as-prepared Cu nanowire mesh 16 on a temporary supporting substrate 17. Synthesis with a solution-based nucleation-and-growth mechanism allowed growth of the Cu nanowires 15 up to about 50 µm in maximum length, leading to a highly-networked mesh form. Certain details of the synthesis of the Cu nanowire mesh 16 are discussed below. X-ray diffraction (XRD; Normal Powder X-ray Diffractometer; RIGAKU, D/MAX-2500, about 40 kV about 300 mA) analysis of the nanowire mesh 16 of FIG. 1 indicated the crystallographic structure of the Cu nanowire mesh, where the diffraction peaks implied the cubic forms of metallic Cu (ICDD, #00-004-0836). The optical images and XRD analysis for as-prepared Ag nanowires 15 (maximum length: about 250 µm) were similarly obtained.

Figure 2:
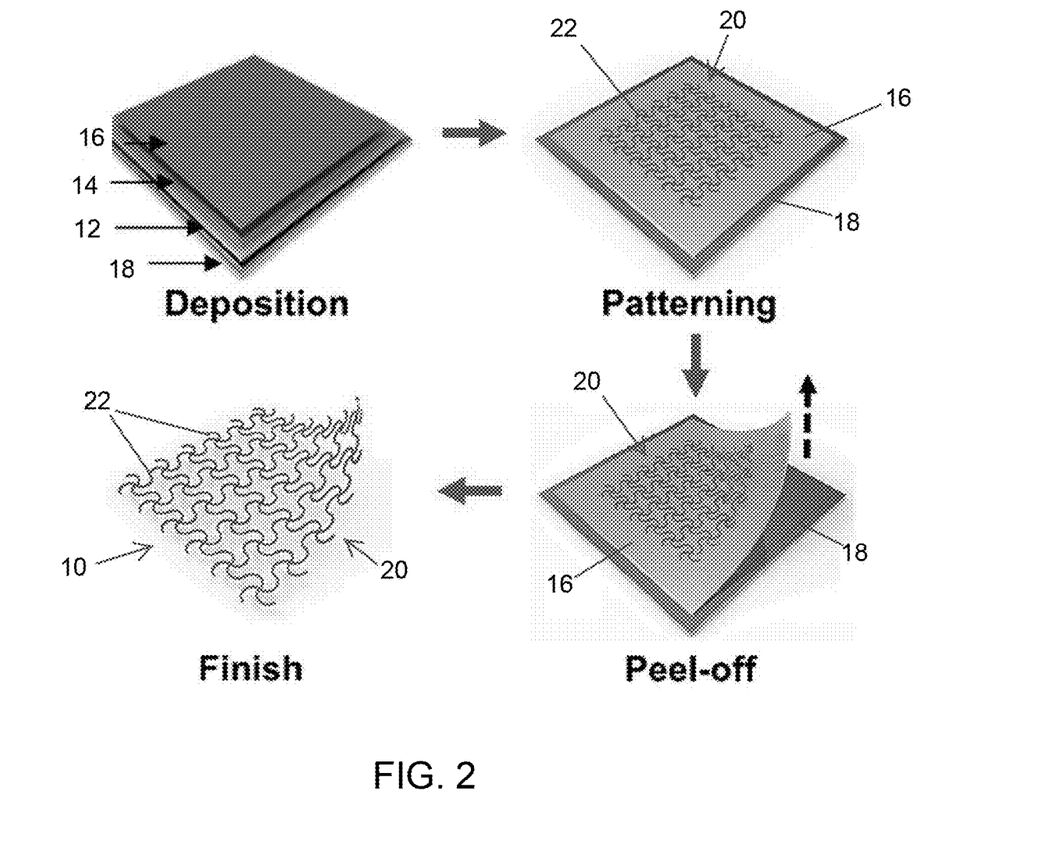
FIG. 2 schematically illustrates steps that may be used in the fabrication of a flexible nanocomposite elastomer structure suitable for use as or in skin-mountable electronic devices in accordance with a nonlimiting embodiment of the present invention, wherein the structure is in the form of a deformable open grid pattern comprising individual interconnected traces that are connected to each other and oriented transverse to each other, and each trace comprises an electrically-conductive nanowire mesh layer that overlies and directly contacts an elastomeric layer.

FIG. 2 represents a schematic illustration of nonlimiting method steps suitable for the construction of an electronic device comprising a nanocomposite elastomer structure 10 of a type described above. The represented fabrication process begins by stacking an intermediate thin film 12 (300 nm thick), an elastomeric thin film 14 (300 nm thick), and nanowire mesh layer (thin film) 16 (600 nm thick) on a temporary support substrate 18. In investigations reported herein, the intermediate thin film 12 was nickel (Ni), the elastomeric thin film 14 was D-PI, and the support substrate 18 was a silicon (Si) wafer, though the use of other materials is foreseeable. Photolithographic patterning and dry etching may be used on the stack of thin films to define a variety of elastically deformable pattern 20 of the nanocomposite elastomer structure formed by the nanowire mesh thin film 16 and elastomeric thin film 14, for example, one or more filamentary serpentine traces 22. The stacked film structure (Si wafer/Ni/D-PI/NW mesh), comprising the patterned traces 22 of the nanocomposite elastomer structure, then undergoes a treatment to promote the removal of the Ni intermediate thin film 12 and patterned traces 22 from the substrate 18. In investigations reported herein, the stacked film structure was immersed in deionized water at room temperature, followed by a mechanical peeling of the thin film layers (Ni/D-PI/NW mesh) from the substrate 18. The ductile Ni intermediate thin film 12 served as a strain inducer that can mechanically deform molecular bonding at the interface with the Si substrate 18, thereby inducing electrostatic charges to attract water molecules. Subsequent chemical reactions facilitated mechanical debonding at significantly decreased peeling energies, enabling intact delamination of the thin film layers from the Si substrate 18. The basic mechanism of this process relied on a water-assisted subcritical debonding phenomenon. The Ni intermediate thin film 12 of the delaminated thin film structure was then removed by immersion in iron chloride ($FeCl_3$) for about thirty seconds to yield an ultra-thin (less than one micrometer-thick) nanocomposite elastomer structure 10 (D-PI/NW mesh) comprising the pattern 20 of traces 22. Further details of the fabrication procedures are discussed below.

Figure 3:
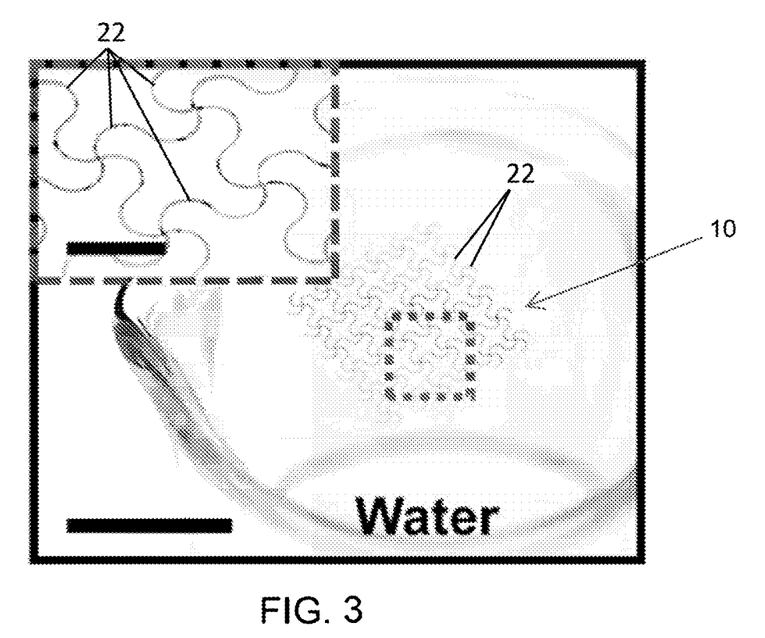
FIG. 3 contains optical images of a nanocomposite elastomer structure configured as shown in FIG. 2 and shown afloat on the surface of water, wherein one of the images is an enlarged inset image in which a filamentary serpentine unit can be seen (scale bars are 1 cm or 1.5 mm (inset)).

FIG. 3 contains images showing a completed nanocomposite elastomer structure afloat on the surface of water by surface tension, facilitating easy transfer of the structure onto the skin of a user. From these images, it can be seen that the pattern (e.g., 20 of FIG. 2) of the nanocomposite elastomer structure is a deformable open grid pattern made up of individual interconnected traces (e.g., traces 22 of FIG. 2), each of which is a filamentary serpentine trace having repetitive oscillations. Furthermore, the individual interconnected traces are arranged in transverse sets of traces that are connected to each other. In the particular embodiment shown, these connections are located at midpoints between adjacent peaks of repetitive oscillations of individual traces.

Figure 4A:
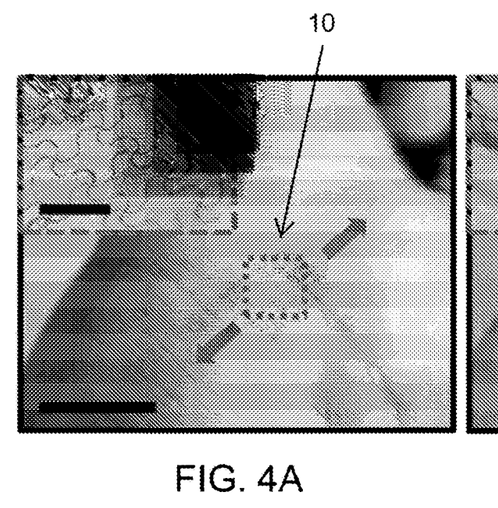
FIGS. 4A and 4B contain optical images showing a nanocomposite elastomer structure configured as shown in FIG. 2 and in use as a skin-mountable electronic device applied to the skin of a human wrist in an extension position (FIG. 4A) and a flexion position (FIG. 4B), wherein enlarged inset images within the images evidence highly intimate contact with the skin maintained during the resulting mechanical deformations of the nanocomposite elastomer structure (scale bars are 1 cm or 2 mm (inset)).
Figure 4B:
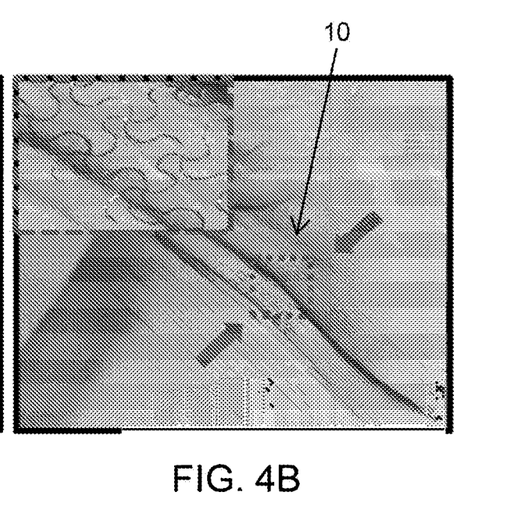

FIGS. 4A and 4B contain images showing the subsequent transfer of the structure 10 onto the wrist of a user. As shown, the structure 10 maintained a high level of conformal contact to the skin throughout the complete stretching (FIG. 4A) and contraction (FIG. 4B) of the skin without any adhesive agent (e.g., spray-on-bandage). When subsequently detached from the skin, the structure 10 collapsed on itself due to its deformability, as is also often observed in traditional ultra thin skin-mountable electronic devices. It is foreseeable that the nanocomposite elastomer structure 10 may have a relatively thicker (for example, greater than about 100 µm thick) form as a result of further comprising various soft packaging materials that encapsulate the D-PI/NW mesh film stack to promote the reusability of the structure 10.

Figure 5A:
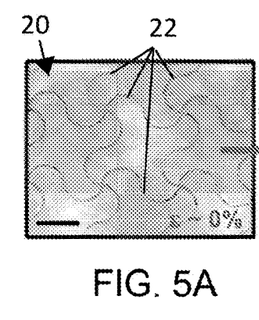
FIGS. 5A, 5B, and 5C contain optical images showing a nanocomposite elastomer structure configured as shown in FIG. 2 and subjected to different tensile strains at 0% (FIG. 5A), 55% (FIG. 5B), and 80% (FIG. 5C) (scale bar of 500 μm).
Figure 5B:
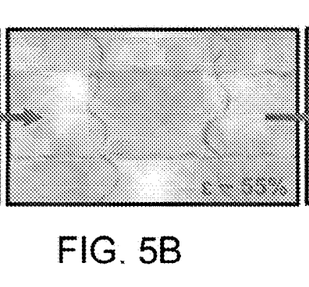
Figure 5C:
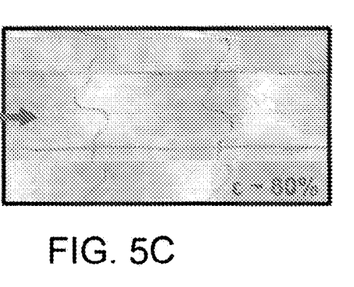
Figure 6A:
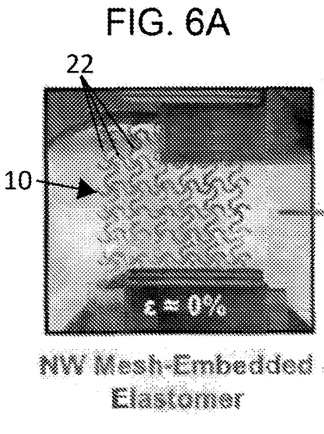
FIGS. 6A, 6B, and 6C contain optical images showing a nanocomposite elastomer structure configured as shown in FIG. 2 and at sequential applied strains of 0%, 80%, and then 0% (scale bar of 4 mm), and FIGS. 6D, 6E, and 6F contain optical images showing a control bare elastomer at sequential applied strains of 0%, 55%, and then 0% (scale bar of 4 mm), evidencing that the nanocomposite elastomer structure did not sustain permanent damage and returned to its original geometry upon releasing the 80% applied strain, whereas the bare elastomer sustained permanent damage as a result of plastic deformation and did not return to its original geometry upon releasing the 55% applied strain.
Figures 6B, 6C:
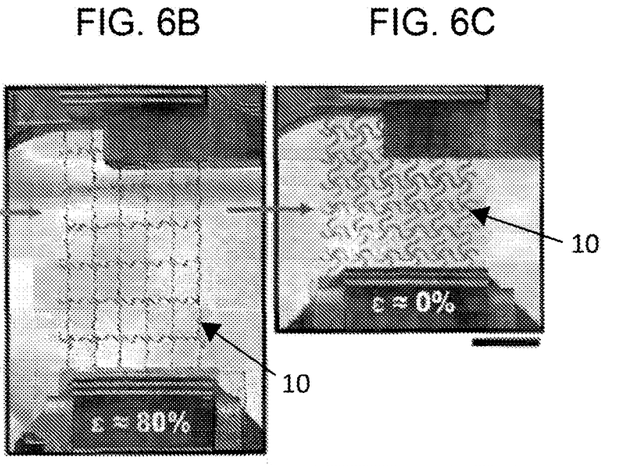
Figure 6D:
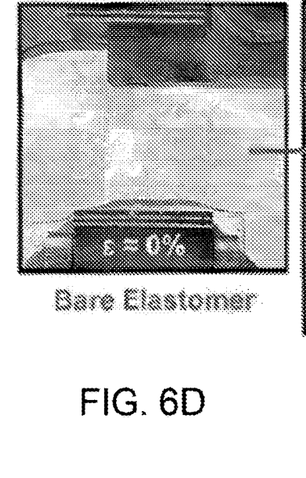
Figure 6E:
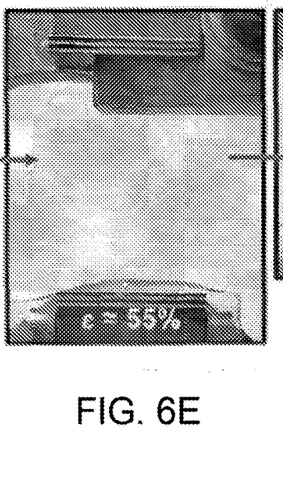
Figure 6F:
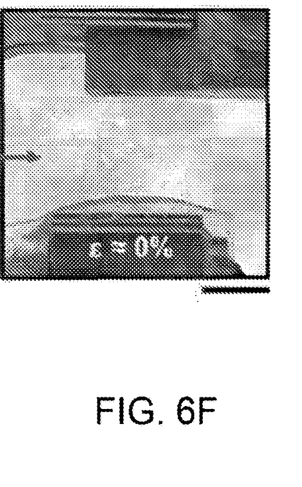

The materials and structural patterns of nanocomposite elastomer structures of the type described above indicated a reduced induced strain during large deformations under stretching. FIGS. 5A, 5B, and 5C show a series of optical images of a nanocomposite elastomer structure 10 under stepwise tensile strain ($\varepsilon$) at about 0%, 55%, and 80%. The results show that the structure 10 could be stretched up to about 80% without any evidence of plastic deformations or fractures, likely due to the excellent mechanical strength and elongation capacity of the embedded highly-networked nanowires 15. FIGS. 6A through 6F contain a comparison of stepwise tensile strain induced in a nanocomposite elastomer structure 10 of this invention (FIGS. 6A, 6B, and 6C) and, for comparison, a bare elastomer structure (without any embedded nanowire mesh layer) patterned into the same geometry (FIGS. 6D, 6E, and 6F). The images show that the bare elastomer structure exhibited non-recoverable plastic deformations when stretched by more than 55%. These experimental results agreed well with a finite element analysis (FEA), confirming that the maximum principle strains in a single trace unit of a nanowire mesh layer are still below the fracture limit of the networked Cu nanowires (about 30%) up to at about 80% stretch, while a traditional Cu thin film-embedded structure fractured at about 55% stretch when the local strain exceeded the fracture limit (about 12%).

In further investigations, experimental results of stress-strain curves obtained from a dynamic mechanical analyzer (DMA, TA Instruments, Q800, about 10 kPa/min) for a Cu nanowire mesh-embedded nanocomposite elastomer structure (of the type shown in FIG. 3), a Cu thin film-embedded elastomer, and a bare elastomer indicated that the maximum strains (before fracture) of the nanowire mesh-embedded nanocomposite elastomer structure were approximately 20% higher than those of the thin film-embedded elastomer and bare elastomer while the effective tensile moduli are similar (about 200 kPa) for all cases. In addition, testing of the electrical connections between individual traces of a Cu nanowire mesh-embedded nanocomposite elastomer structure of the type shown in FIG. 3 evidenced that the electrical connections were maintained at a tensile strain ($\varepsilon$) of about 80% over about 1000 repetitive cycles without significant degradation. Two of the evaluated specimens contained different densities of the nanowire mesh layer. The resistance of the lower-density specimen (about 0.5 g/m$^2$) slightly increased after about 500 loading cycles whereas the higher-density specimen (about 1.0 g/m$^2$) retained a consistent resistance of about 30 $\Omega$ through the entire cycles, implying that more networked nanowires can reduce the possibility of disconnected conducting paths. Additional investigations showed that nanocomposite elastomer structures of the type shown in FIG. 3 exhibited enhanced crack resistance due to the randomly oriented junctions of nanowires that suppress the initiation and propagation of cracks, and that absolute electrical resistances of nanocomposite elastomer structures of the type shown in FIG. 3 almost fully recovered following cyclic elongations under repetitive applied strains of up to about 80%.

The mechanism of well-maintained electrical conduction in the nanowire mesh-embedded nanocomposite elastomer structures was concluded to involve the characteristic deformations of the highly-networked nanowires under stretching. For instance, at low strains, the nanowires changed their shapes by aligning themselves to the applied strain direction, and thereby efficiently accommodated mechanical deformations without significant degradations in the conduction path. Beyond the failure limits ($\varepsilon$>80%), the networked nanowires began to partly rupture rather than the catastrophically crack (as typically observed in thin films), and thereby the intact nanowires were still able to serve as an electrical conduction path. An FEA simulation indicated the underlying mechanism of this advantage. When stretched, the randomly oriented Cu nanowires slide against each other and rotate to the stretching direction. This extra degree of freedom in the nanowires allows release of strain energy and prevents singular deformations at the junctions. Therefore, although each single Cu nanowire has a fracture limit of about 3.0%, which is much smaller than that of a Cu thin film (about 12%), the networked nanowires can sustain up to about 30% local strain before fracture. Further details of the FEA simulation are discussed below. It is noteworthy that the sliding events of nanowires affect the contact resistance at the nanowire junctions, resulting in changes of resistance. Incorporating the structural serpentine patterns (traces) promote suppression of such influence by distributing the induced strains in a wider region of the deformed meanders instead of being concentrated in a small region. The strain insensitivity provides a beneficial attribute for various devices, such as electrophysiological electrodes and temperature monitors, as a result of being less sensitive to motion-induced strains of users.

The mechanical strength in normal and shear directions is particularly important for various skin-mountable electronic devices where excessive normal and shear stresses can drive delamination of the entire device. Experimental measurements of normal forces were obtained from a mechanical T-peeling tester equipped with a high-resolution force gauge (Mark-10, Copiague, N.Y., Resolution: ±0.25%) for a Cu nanowire mesh layer (1.0 g/m$^2$) and a control Cu thin film (about 600 nm thick) integrated onto an artificial synthetic skin (Ecoflex, E of about 125 kPa, about 2 mm thick, modulated with human skin-like textures). A strong adhesive electrical insulation tape (Tapes Master, KP-1M-36-12) allowed initiation of the peeling at a constant rate of 1 mm/min at about 90° to the surface. The results clearly showed that the initial peak peeling force near the edges of the nanowire mesh-embedded nanocomposite elastomer structure (about 1.4 N) was almost three-fold higher than that of the thin film-based elastomer (about 0.5 N), most likely due to the significantly increased surface contact areas of the nanowire mesh layer. The experimental measurements of the surface topography obtained from an atomic force microscopy (AFM, Asylum Research, MFP-3D) showed that the surface areas of the Cu nanowire mesh layer were more than 1000 times higher than those of the Cu thin film. An enhanced initial peak peeling force is highly desirable for any skin-mountable device because the propensity for delamination exists mostly at/near edges due to concentrated stresses. Optical and scanning electron microscope (SEM) images showed the ability of nanowire mesh-embedded nanocomposite elastomer structures to adhere seamlessly to the surface of artificial skin with a high level of conformality, in other words, the structures followed most of the topography of the surface and penetrated to the deepest creases and pits.

Figure 7A:
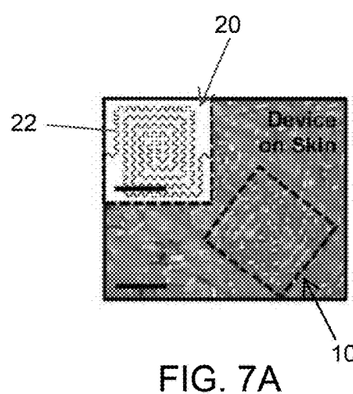
FIG. 7A contains two optical images of a nanocomposite elastomer structure (scale bars are one cm) suitable for use in a skin-mountable electronic thermotherapy device in accordance with another nonlimiting embodiment of the present invention, wherein the structure is in the form of a deformable open serpentine pattern comprising a single trace comprising an electrically-conductive nanowire mesh layer that overlies and directly contacts an elastomeric layer.
Figure 7B:
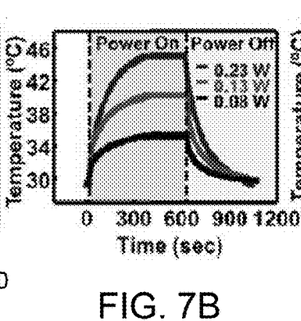
FIG. 7B is a graph containing experimental results of average temperatures generated with a thermotherapy device configured as shown in FIG. 7A as a result of incident powers 0.08 W, 0.13 W, and 0.23 W.

The desirable mechanical properties described above provide platforms for applications in a broad range of skin-mountable electronic devices. FIG. 7A shows a representative nonlimiting example of a skin-like thermotherapy device (patch) comprising an nanocomposite elastomeric structure 10 that contains a Cu nanowire mesh layer (about 1.0 g/m$^2$, 600 nm thick) and a D-PI elastomeric layer (300 nm thick). The mesh layer is configured to serve as a Joule-heating element of the device. The nanocomposite elastomeric structure has been fabricated to comprise a serpentine pattern 20 to efficiently accommodate induced strains under mechanical deformations. However, in contrast to the nanocomposite elastomeric structures shown thus far in the drawings, the device shown in FIG. 7A is a nanocomposite elastomer structure comprising a single serpentine trace 22, as most readily seen in the inset image. FIG. 7B shows temperature distributions obtained with an infrared (IR) camera (FLIR SC645, sensitivity: 0.05° C.), on the skin of a knee heated by the thermotherapy device to which power levels of 0.08 W, 0.13 W, and 0.23 W were supplied by an external wire connection. The temperature increases are seen as linearly proportional to the incident power, and therefore can allow the controlled operation of thermotherapy device.

Figure 7C:
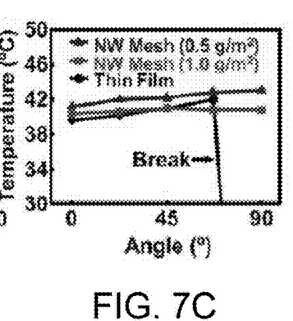
FIG. 7C is a graph containing experimental results of heat generated with two thermotherapy devices configured as shown in FIG. 7A and applied to a human knee under bending from 0° to 90°.

FIG. 7C shows experimental demonstrations with activated devices that contain Cu nanowire mesh-embedded nanocomposite elastomer structures (0.5 g/m² and 1.0 g/m²) and a control thin film-embedded elastomer, all mounted on a knee undergoing bending (θ=0° to 90°). Here, the elevated temperature aims to maintain constantly at 40° C. to 42° C. by modulating the incident powers (0.1 W to 0.8 W) for which the final temperature remained below the maximum allowable temperature (about 45° C.) in human tissues to prevent any possible damage. The results also show that the nanowire mesh-embedded nanocomposite elastomer structures maintained the elevated temperature under the complete bending angle (θ) up to about 90°, whereas the thin film-based devices failed at θ=about 60°, typically due to plastic deformations or catastrophic cracks. These results illuminated a potential utility as a reliable means to provide therapeutic heat through mechanically compliant contacts on the joints without significant constraints on natural movements.

Figure 8A:
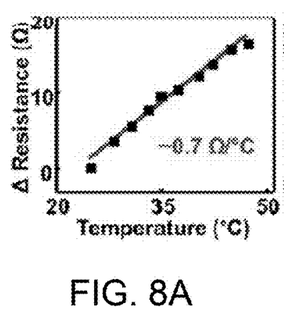
FIG. 8A is a graph containing experimental results indicating the change in resistance as a function of temperature for a thermotherapy device configured as shown in FIG. 7A, wherein the slope denotes a sensitivity of the sensor (about 0.7 Ω/° C.).
Figure 8B:
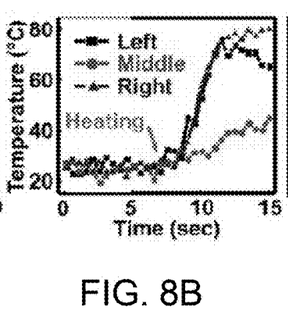
FIG. 8B is a graph containing experimental results obtained with a thermotherapy device shown in FIG. 8C (scale bar of one mm), wherein the device comprises a 1×3 array of nanocomposite elastomer structures each configured as shown in FIG. 7A, and the results of FIG. 8B represent temperature mapping obtained by placing preheated objects on the lefthand and righthand nanocomposite elastomer structures of the array as seen in the IR image in FIG. 8C.
Figure 8C:
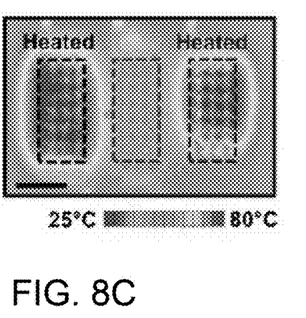

Similar structures can be extended to build a temperature sensor by exploiting a predictable change in resistance of a nanowire mesh-embedded nanocomposite elastomer structure that occurs as a result of a change in environmental temperature. FIG. 8A shows a characterization curve for a representative Cu nanowire mesh-embedded nanocomposite elastomer structure temperature sensor in the absence of an applied mechanical strain, where the slope indicates sensitivity (about 0.7 Ω/° C.). Arrangement of multiple heating elements allows an array of sensors to be formed for mapping temperature in a spatial manner. FIG. 8B presents results of temperature mapping obtained from a 1×3 array of nanocomposite elastomer structures each configured as shown in FIG. 7A, and the IR image of FIG. 8C represents temperature mapping obtained by placing preheated objects on the lefthand and righthand nanocomposite elastomer structures of the array as seen in the IR image of FIG. 8C. After placement on an artificial skin, the lefthand and righthand nanocomposite elastomer structures of the array were selectively preheated (110° C. for about 10 min) with pieces of glass in a room temperature environment. The temperatures of the lefthand and righthand structures reached 70° C. to 80° C. within about five seconds upon heating, whereas the temperature of the middle structure remained below about 40° C. These results corresponded well with observations with an IR camera seen in FIG. 8C, where the highlighted areas (dashed boxes) indicate the pre-heated locations during the test. The change of resistance would be affected by mechanical strains from the natural motions of wearers, and therefore simultaneous monitoring of strain and temperature may be necessary to compensate the correlation.

Figure 9:
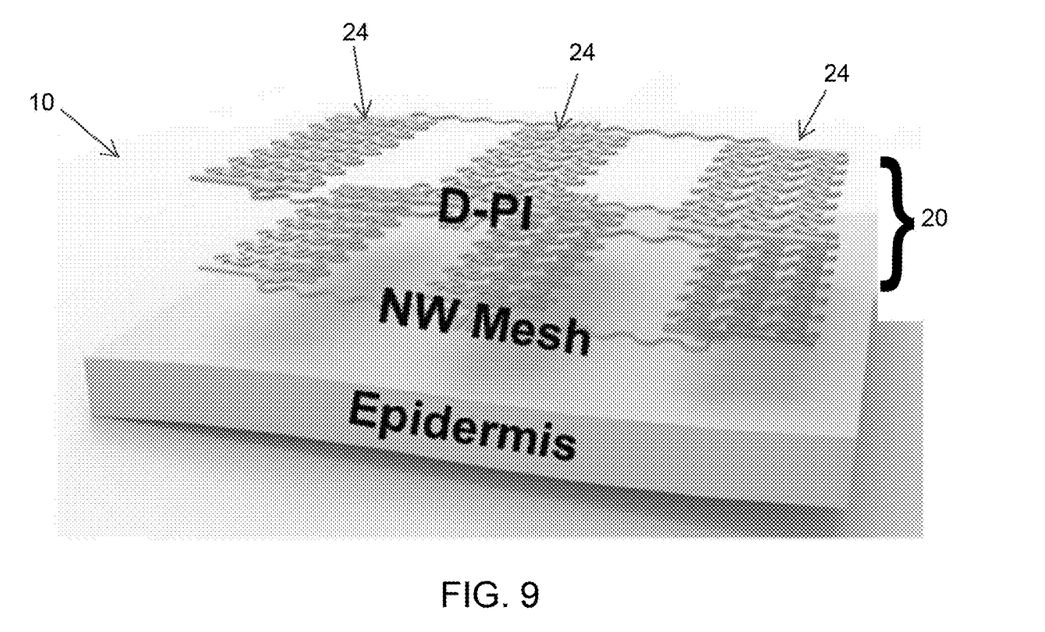
FIG. 9 is an exploded schematic view of a nanocomposite elastomer structure suitable for use in a skin-mountable electronic electrophysiological monitoring device in accordance with another nonlimiting embodiment of the present invention, wherein the structure comprises three units each similar in the form to the deformable open grid pattern of FIG. 2.
Figure 10:
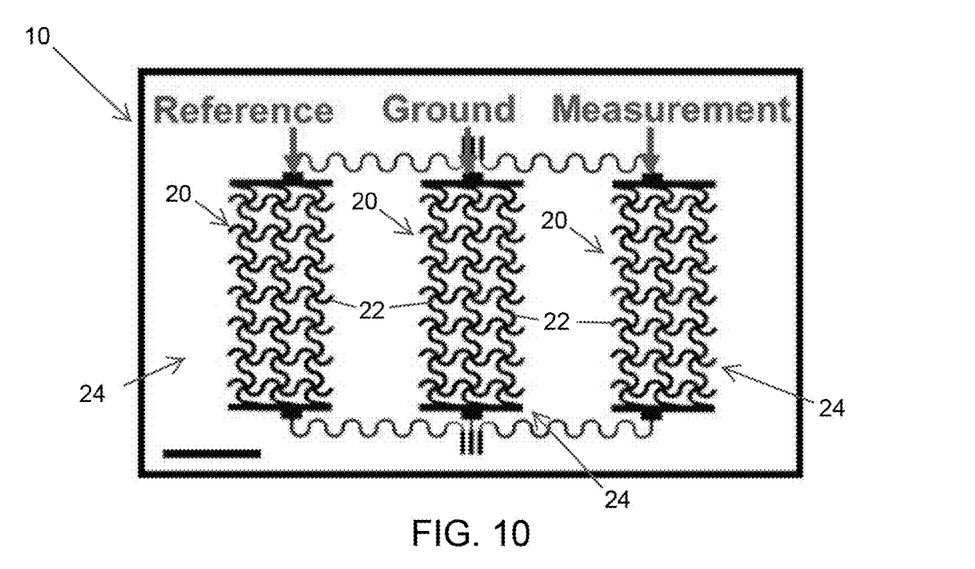
FIG. 10 contains an optical image of an electrophysiological monitoring device configured as shown in FIG. 9, wherein the units are labeled as reference, measurement, and ground electrodes (scale bar of 5 mm).

As another nonlimiting application example, FIGS. 9 and 10 represent a schematic illustration and an optical image of a skin-like electrophysiological monitoring device. The device includes a nanocomposite elastomer structure 10 comprising a thin film of Cu nanowire mesh layer (1.0 g/m2) on a D-PI film (300 nm thick) patterned to form three separate units 24, each comprising a pattern 20 of filamentary serpentine traces 22. Each unit 24 serves as a reference, ground, or measurement electrode (from the left) that can be directly coupled to the skin, as represented in FIG. 9. This arrangement allowed for high quality recordings of electrocardiograms (ECG) and electromyograms (EMG) by applying the device on the chest and the forearm of a volunteer. The resulting ECG and EMG data obtained with the Cu nanowire mesh-based electrodes were qualitatively comparable to those recorded with control Cu thin film-based electrodes. Consistent with the above-mentioned results, the Cu nanowire mesh-based electrodes exhibited excellent stretchability up to a strain (ε) of about 80% before fracture, while the control Cu thin-film based electrodes typically failed at a strain of about 40 to 50%.

The following contains further details of methods utilized to analyze and fabricate test specimens that were evaluated during investigations discussed above in reference to FIGS. 1 through 10.

Finite element analysis (FEA): Networked Cu nanowires were modeled by a representative unit of a deformable open grid pattern of a type shown in FIG. 3. The unit consisted of four networked Cu nanowires (Young's modulus of 119 GPa, Poisson's ratio of 0.33) in a rectangular shape to account for random orientations. The nanowires were bonded to an elastomer substrate (Young's modulus of 60 kPa, Poisson's ratio of 0.49) that was modeled as a Neo-Hookean hyperelastic solid. A typical coefficient of friction of 0.29 was adopted to simulate friction between the nanowires. The FEA model showed that the maximum strain in the nanowires reached the fracture limit of 3.0% when the networked nanowires were stretched by 30%, implying that the networked nanowires can sustain local strain of up to 30%. This criterion was then applied to a full model in the studies where the nanowire mesh-embedded traces were modeled as a continuum film for which fracture occurred when the local strain reached 30%.

Fabrication of a Cu nanowire mesh: A conventional solution-based nucleation and growth mechanism was used for the synthesis of Cu nanowires. A mixture of sodium hydroxide (NaOH) powders (45 g, Sigma Aldrich) and copper nitrate ($Cu(NO_3)_2$) solution (0.05 g, Sigma Aldrich) was dissolved in 80 mL of deionized water with vigorous stirring. Aqueous solutions of ethylenediamine (EDA, 0.5 mL, Sigma Aldrich) and hydrazine (100 mL, 35 wt.% in H2O, Sigma Aldrich) were added to the solution to chemically functionalize the surface and prevent oxidation of the Cu nanowires, respectively. The chemical reaction changed color of the solution from blue to transparent within about five minutes. Heating the mixture solution at 60° C. for one hour, without stirring, lifted a reddish layer of Cu nanowires on the surface of the solution. Repeated centrifuges (Eppendorf, 5417R, about five times) at 2000 rpm for five minutes separated the Cu nanowires from remaining slurry. The refined Cu nanowires were mixed with 20 mL of isopropanol (99.5%, Sigma Aldrich) in a glass vial, and then filtered through a Teflon filter (SterliTech, 0.2 μm pore size) by use of a vacuum pump (KODIVAC GHP-240, about 104 Torr). Complete drying at room temperature for about five minutes formed a thin layer of Cu nanowire mesh on the surface of the Teflon filter. The resulted single Cu nanowire exhibited approximately 40-50 μm in length and 80-120 nm in diameter with aspect ratio of greater than about 400. The upside-down Teflon filter was firmly pressed onto a receiver substrate to transfer the Cu nanowire mesh. Gentle removal of the Teflon filter completed the entire process.

Fabrication of an Ag nanowire mesh: A conventional solution-based multi-step growth mechanism was used for the synthesis of Ag nanowires. The synthesis began with preheating of 50 mL of ethylene glycol (EG, J. T. Baker, 9300-03) in an oil bath (Chemglass Inc., CG-1100) at about 150° C. for one hour. 400 μL of copper (II) chloride ($CuCl_2$, 4 mM, Sigma-Aldrich, 487847) and 15 mL of polyvinylpyrrolidone (PVP, 0.147 M, Sigma-Aldrich; 856568) were added in the preheated EG at an interval of fifteen minutes. Injection of silver nitrate ($AgNO_3$, 15 mL, 0.094 M) at a rate of one mL/min performed with a syringe pump (World Precision Instruments, AL-4000) changed the color of the aqueous solution from ivory to grey. Successive growth steps by repeating these procedures increased the lengths of the Ag nanowires up to about 250 µm maximum. All other fabrication procedures to form a mesh structure were similar to those described for the Cu nanowire mesh.

Figure 11:
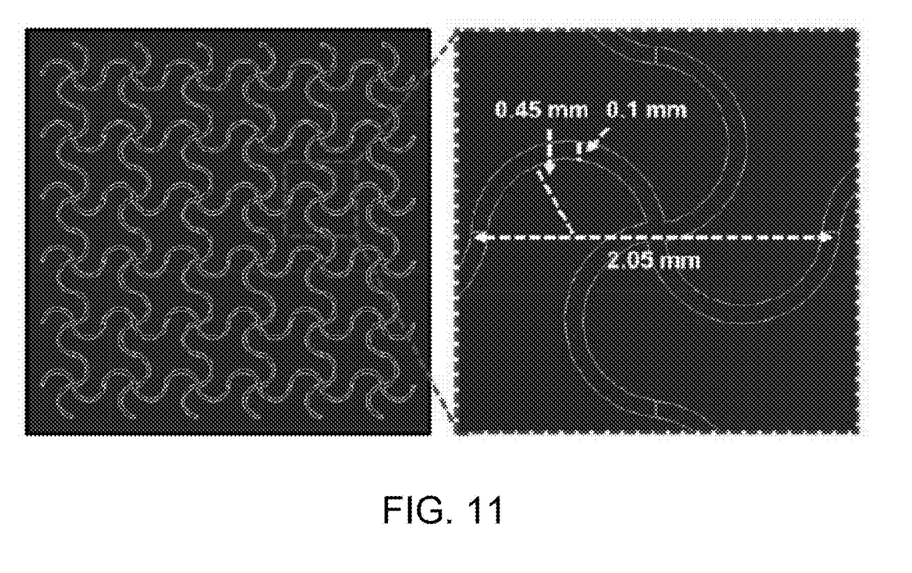
FIG. 11 represents a Cu thin-film elastomer structure that was prepared for comparative testing against nanocomposite elastomer structures similarly configured to the structure shown in FIG. 2.

Fabrication of Cu thin-film elastomer structures: Fabrication began with depositing Ni (about 300 nm thick) and casting a D-PI (about 300 nm thick) layer onto a Si wafer using an electron-beam evaporator and spin-coater, respectively. A layer of the Cu thin film (about 600 nm thick) was deposited by sputtering. Photolithographic patterning by use of a photoresist (Clariant AZ5214, 3000 rpm, 30 sec) with 365 nm optical lithography and wet etching with Cu etchant (Transene) defined open grid serpentine patterns as a stretchable design. A schematic illustration of a representative pattern appears in FIG. 11, showing certain geometric details. Additional casting of a layer of poly(methyl methacrylate) (PMMA, about 800 nm thick) was formed on top of each pattern to serve as a temporary protection layer from the environment Immersion of the entire resulting structure in water at room temperature followed by gentle mechanical peel-off with a temporary holder, such as thermal release tape (Nitto Denko, Inc.), separated the stacked layers (Ni/D-PI/Cu thin film/PMMA/thermal release tape) from the Si wafer. The delaminated Ni layer on the bottom was eliminated by immersion in iron chloride ($FeCl_3$) for about thirty seconds. Heating at 100° C. for about one minute removed the adhesion of the thermal release tape to release the remaining layers. Immersion in acetone eliminated the PMMA layer. The completed structure was then transferred onto water, allowing its retrieval onto target surfaces of interest.

Fabrication of Cu nanowire mesh-embedded nanocomposite elastomer structures: The fabrication began with depositing Ni (about 300 nm thick) and casting a D-PI film (about 300 nm thick) on a Si wafer by using electron-beam evaporator and spin-coater, respectively. A layer of the as-prepared nanowire mesh was transferred on top of this structure by using methods described above. Photolithographic patterning and wet etching through the layers defined open grid patterns as a stretchable design. All other fabrication procedures were similar to those described above for the Cu thin-film composite elastomer structures.

Fabrication of artificial synthetic skin: Commercially available biocompatible silicone-based elastomers such as Dragon Skin (Dragon Skin 30, Smooth-On, Inc.) and Ecoflex (Ecoflex 30, Smooth-On) were used to fabricate an artificial skin. The Dragon Skin (1:1 ratio of part A and B by weight) was mixed with flesh tone silicone pigment (Slic Pig, Smooth-On, Inc., 3% by wright) to modulate the color. Degassing in a vacuum desiccator for about fifteen minutes eliminated entrapped air. Pouring the prepared mixtures onto the forearm of a volunteer followed by curing for one hour at room temperature defined the human skin-like textures onto the surface to serve as a mold. The fully cured layer was carefully peeled off and placed in a clean petri dish with textured surface up in the air. Another casting and peel-off of 1:1 ratio (part A and B by weight) of Ecoflex onto the mold completed the entire process.

Nanocomposite elastomer structures disclosed herein as having a mesh layer of highly-networked nanowires combined with an ultra-thin elastomeric layer offer a simple means to enhance the mechanical properties for a broad range of skin-mountable electronic devices capable of maintaining robust contact with skin during dynamic motions. Such structures raise the mechanical and electrical reliability of their corresponding systems against potential fracture and delamination by improving overall crack resistance, contact adhesion, and normal/shear strength. Experimental and simulation results revealed the underlying mechanisms of the observed behaviors and suggest opportunities to achieve a range of skin-coupled electronic systems. The basic concepts of these structures and investigations are applicable to other classes of stretchable electronics by offering solutions for mechanical durability against mechanically harsh environments. On the basis of experimental and simulation results reported herein, suitable thicknesses for nanowire mesh layers of the nanocomposite elastomer structures were concluded to be about 100 nm to about 5 micrometers, and suitable thicknesses for the elastomeric layers were concluded to be about 100 nm to about 100 micrometers, particularly about 100 nm to about 50 micrometers, and more preferably about 100 nm to about 10 micrometers, yielding structures having a total thickness of about 100 nm to about 100 micrometers, particularly about 100 nm to about 50 micrometers, and more preferably about 100 nm to about 15 micrometers.

Figure 12:
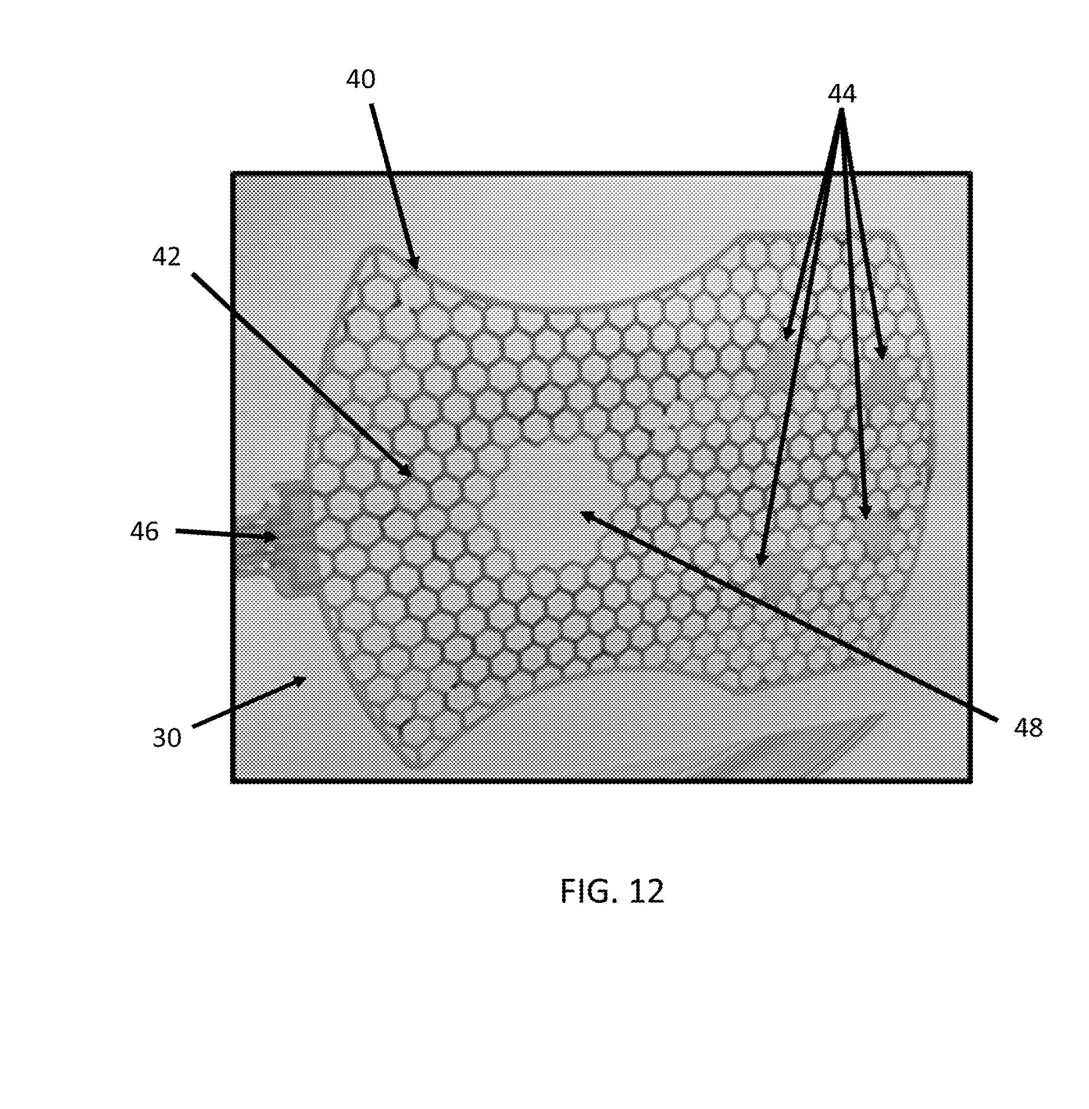
FIG. 12 contains an image of a composite elastomer structure configured as a skin-mountable electrophysiological monitoring device for measuring muscle activity within the neck of a human body in accordance with another nonlimiting embodiment of the present invention.

FIG. 12 represents an alternative to the nanocomposite elastomer structures discussed above in reference to FIGS. 1 through 10. In particular, FIG. 12 represents a skin-mountable electronic device that includes a composite elastomer structure 30 that may be fabricated to comprise a pattern 40 of individual interconnected traces 42 each comprising an electrically-conductive layer that overlies and directly contacts an underlying biocompatible elastomeric layer. The electrically-conductive layer may be formed of a patterned metallic thin film instead of the patterned nanowire mesh described above for the nanocomposite elastomer structures of FIGS. 1 through 10, though it should be understood that the electrically-conductive layer could be formed of a patterned nanowire mesh. The elastomeric layer provides a supporting substrate for the pattern of interconnected traces 42 that also preferably contributes a degree of flexibility and/or stretchability to the device and allows the device to conform to contours of the human body. Examples of suitable biocompatible materials for the elastomeric layer include silicone-based elastomers, as nonlimiting examples, polyimides, polydimethylsiloxane (PDMS), and silicones, including but not limited to silicones commercially available under the names Silbione® and Ecoflex®.

The device represented in FIG. 12 is particularly well suited as an electromyogram (EMG) device for measuring muscle activity in a human body, for example, to collect data relating to muscle activity involved in the act of swallowing, which is one of the most complex sensorimotor functions of the human body and essential for human survival and well-being. Swallowing requires the perfect coordination of more than thirty pairs of muscles of the head and neck, six pairs of cranial nerves, and several brain areas to be completed successfully. Disruptions in any of these structures can result in swallowing disorders (a.k.a. dysphagia).

The patterned composite elastomer structure 30 of the device shown in FIG. 12 is preferably fabricated to exhibit mechanical properties that are well matched to those of the epidermis of the skin, and is thereby able to conformally contact the skin without the need of any adhesive, thus enabling the recording of high-level electromyographic signals. The patterned composite elastomer structure 30 preferably remains stable under repeated stretching and compressing of the underlying skin surface and also preferably achieves a desired level of mechanical adaptability against natural behaviors of a wearer, such as stretching, compressing, twisting, and scratching.

The pattern 40 of individual interconnected traces 42 of the composite elastomer structure 30 shown in FIG. 12 defines a honeycomb-like design that has been determined to meet the mechanical design criteria discussed above. In addition to the pattern 40 of traces 42, the skin-mountable electronic device of FIG. 12 is shown as comprising four functional electrodes 44 located within the pattern 40 and an electrical connector 46 for electrically connecting an electronic unit and power supply to the electrodes 44. The electrical connector 46, for example, a flexible anisotropic conductive film, is electrically connected to each of the electrodes 44 through different conductive paths defined the electrically-conductive layer of certain individual interconnected traces 42 that are serially electrically connected to each other and not electrically connected to the electrically-conductive layer of other traces 42, so that each electrode 44 has a separate electrical connection or path to the connector 46. The device is also represented as including a region 48 that is free of the pattern 40 of individual interconnected traces 42, where a pressure sensor may optionally be incorporated onto the elastomeric layer, for example, a thyroid pressure sensor for verification of swallowing events. The device may further incorporate a thin layer of semiconducting membranes to define strain gauges onto the thyroid/larynx, allowing the characterization of the initiation, relative duration, and completion of a swallow.

The electrodes 44 are positioned and sized on the device to interface with the skin to measure the surface potential of EMG signals that are present on the skin during the muscle activity involved in the act of swallowing. By connecting the electrodes 44 to a suitable power supply, contraction of muscles of a human body contacted by the electrodes 44 causes a voltage differential between any two of the electrodes 44, allowing for the use of a data acquisition system to measure the voltage differential produced between the electrodes 44. Through extensive pre-clinical testing, devices of the type shown in FIG. 12 were designed to have excellent alignment with the submental muscle fibers, essential for consistent placement along the muscle fibers direction, and for increasing signal validity. As a nonlimiting example, the four electrodes 44 shown in FIG. 12 may have an inter-electrode distance of about 1.5 centimeters, which is believed to be optimal for the small muscle lengths in the submental (under the chin) area. The incorporation of the electrodes 44 onto the device overcomes the issue of accurate electrode placement typically seen when using conventional EMG sensors.

In experiments leading to this aspect of the invention, devices of the type shown in FIG. 12 were connected with a wireless unit commercially available from BioRadio, Inc., to link the devices to a software data acquisition and analysis system. It is foreseeable that the device could include additional add-on chips for the purpose of integrating a thyroid pressure sensor and the wireless unit. For example, a thyroid pressure sensor chip and a custom-built miniaturized wireless unit could be mechanically incorporated onto the device shown in FIG. 12. Testing of healthy human subjects can be conducted to compare the data collected via the pressure sensor with data collected with the device and a nasal airflow cannula during swallowing. The nasal airflow/respiratory signal is interrupted during swallowing and thus a straight line on the respiratory signal graph would indicate a swallow event. This signal would provide a validation measure for the occurrence of a swallow and can be used to validate the pressure sensor data. Further it should be recognized that apps can be developed for the recording of data acquired using the device wirelessly and for providing user interfaces for patients and clinicians.

The following nonlimiting method was utilized to fabricate the particular embodiment of the device shown in FIG. 12. The fabrication began with preparing a substrate commercially available from DuPont under the name Pyralux®, comprising a 13 μm copper layer on a 13 μm polyimide film. The substrate was mounted onto a glass panel as a temporary carrier and a laser cutter was used to cut away and define the outline of the structure 30 and its pattern 40 of interconnected traces 42. The patterned composite elastomer structure 30 was thoroughly cleaned with isopropyl alcohol and acetone, after which a layer of a dry film photoresist (DuPont Riston®) was laminated on the copper layer of the structure 30 using a hot roll laminator. A standard photolithographic process was used to define the photoresist, after which the copper layer was patterned chemically with an ammonium persulfate solution. The photoresist layer was then removed with a sodium hydroxide solution and a thin layer of gold was electroplated to encapsulate the exposed copper to prevent oxidation and increase biocompatibility with the skin. An anisotropic conductive film (ACF; Elform, USA) was bonded to the composite elastomer structure 30 to form an electrical connection to an external preamplifier and wireless communication components. Finally, a layer of a silicone elastomer commercially available from Elkem under the name Silbione® was applied as an encapsulant to the composite elastomer structure 30, while leaving the electrodes 44 exposed, to serve as an insulation layer and promote adhesion to the skin.

In view of the above, the skin-mountable electronic device of FIG. 12 provides a non-invasive and ergonomic wearable sensor system capable of improving the management of dysphagia and enabling reliable tele-management of dysphagia treatment. The composite elastomer structure 30 of the device shown in FIG. 12 can be ultra-thin, wearable, and skin-like such that the device can be robustly and comfortably attached to the skin under an individual's chin to provide high quality and reliable EMG signals of the submental muscles during swallowing and swallowing exercises. The materials, design layouts, and circuit configurations of the device are adjustable, and therefore its application can be extended to other disorders affecting the same muscle groups, e.g., speech disorders. On the basis of experimental results, suitable thicknesses for the metal film layer of the composite elastomer structure 30 were concluded to be about 10 to about 25 micrometers, more preferably about 10 to about 15 micrometers, and suitable thicknesses for the elastomeric layer were concluded to be about 10 to about 100 micrometers, particularly about 10 to about 50 micrometers, and more preferably about 10 to about 30 micrometers, yielding structures 30 having a total thickness of about 20 to about 100 micrometers, particularly about 20 to about 50 micrometers, and more preferably about 20 to about 30 micrometers.

Figure 13:
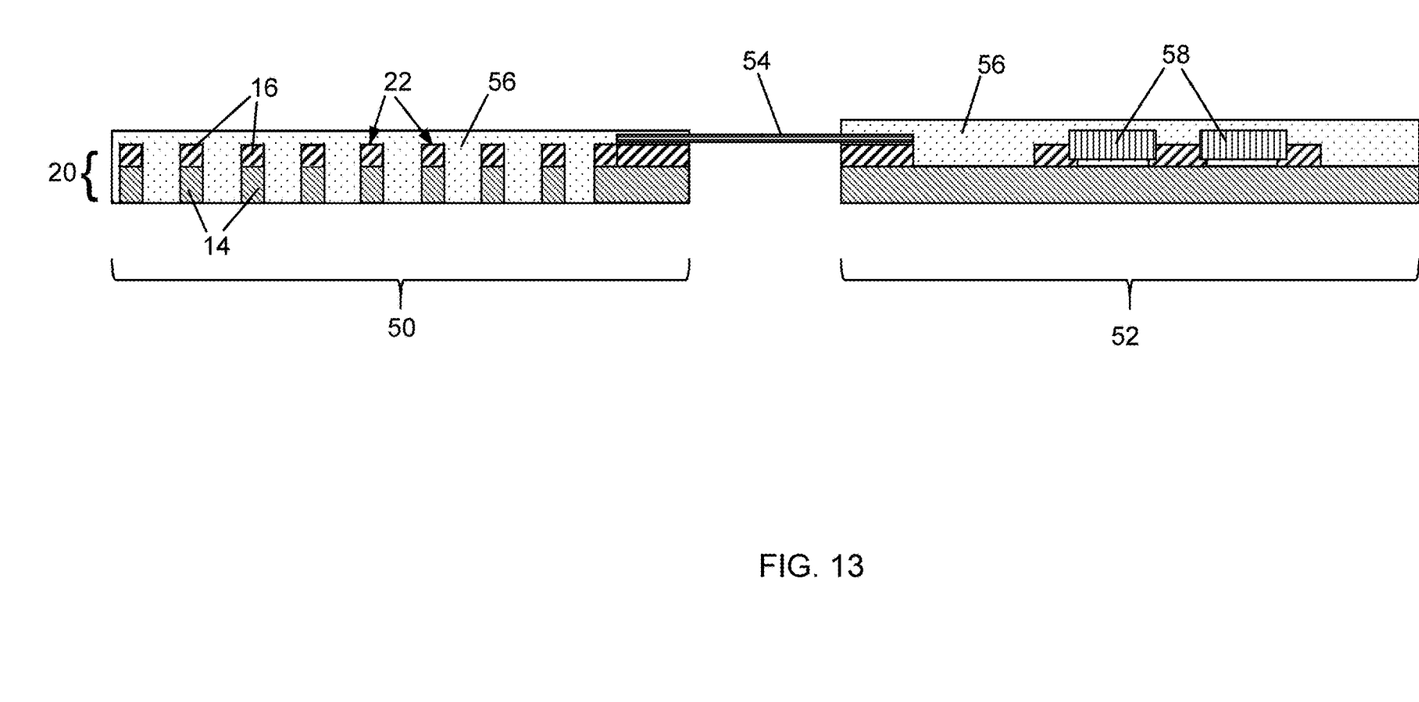
FIG. 13 is a schematic representation showing a cross-sectional view of a system incorporating a wireless unit coupled to any one of the aforementioned nanocomposite or composite elastomer structures.

FIG. 13 schematically represents a system comprising a wireless unit 52 coupled to a skin-mountable elastomer device 50 constructed of a flexible (nanocomposite or composite elastomer) structure (e.g., structure 10 or 30). The wireless unit 52 can be connected to the flexible structure by any suitable means 54 to enable the wireless unit 52 to control and/or receive outputs of the flexible structure. The flexible structure of FIG. 13 is particularly representative of the nanocomposite elastomer structure 10 described for any of the embodiments depicted in FIGS. 1 through 10, though it is foreseeable that the composite elastomer structure 30 of FIG. 12 could be configured to have a cross-section as shown in FIG. 13. Encapsulant materials 56 are depicted in FIG. 13 as encasing the traces 22 of the flexible structure 10 and electronic devices 58 of the wireless unit 52 to mechanically and electrically isolate their electronic components from the skin and environment as well as promote adhesion to the skin. The inclusion of an encapsulant offers the ability to promote signal quality, wearing comfort, and durability of the device.

Figure 14:
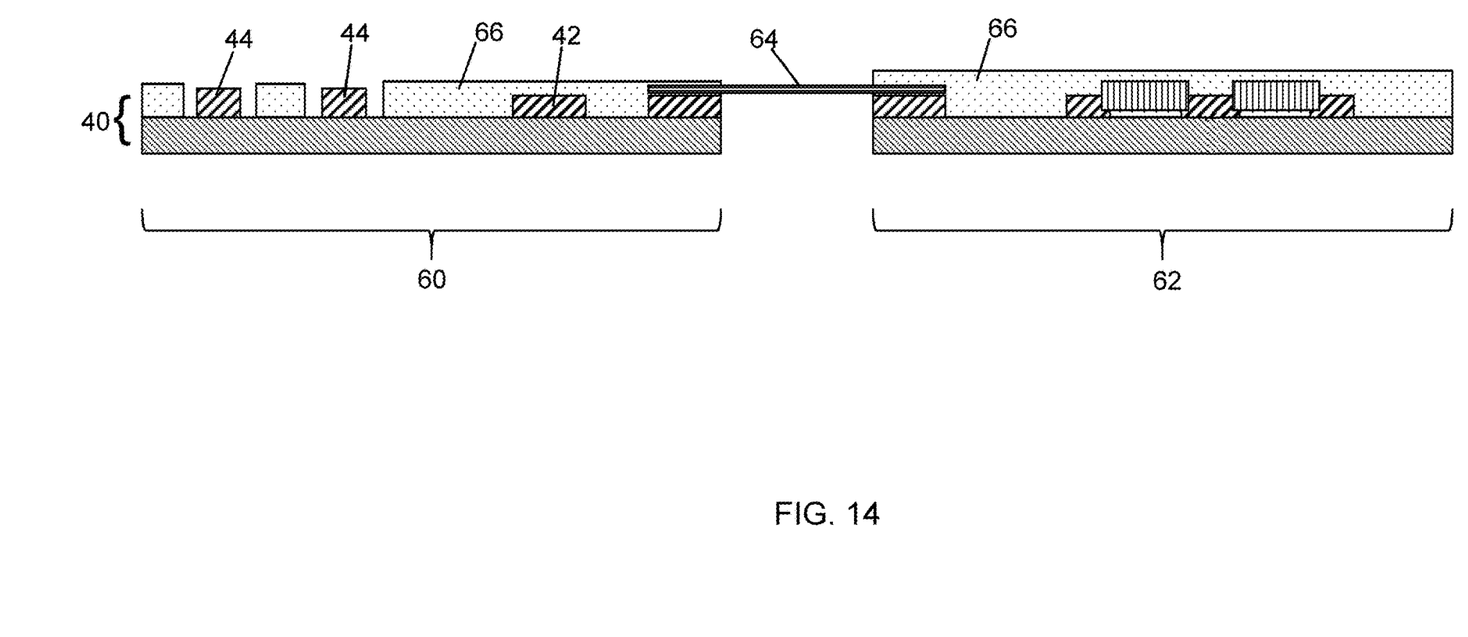
FIG. 14 is a schematic representation showing a cross-sectional view of another system incorporating a wireless unit coupled to any one of the aforementioned nanocomposite or composite elastomer structures.

FIG. 14 is a schematic cross-sectional representation of another skin-mountable elastomer device 60 constructed of a flexible (nanocomposite or composite elastomer) structure (e.g., structure 10 or 30) and incorporated into a system that further includes a wireless unit 62 similar to that described in reference to FIG. 13. The flexible structure of FIG. 14 is particularly representative of the composite elastomer structure 30 depicted in FIG. 12, though it is foreseeable that the nanocomposite elastomer structures 10 of FIGS. 1 through 10 could be configured to have a cross-section as shown in FIG. 14. The device 60 and wireless unit 62 are fabricated on separate but potentially identical elastomeric layers that provide a thin flexible support substrate. The electrodes 44 and pattern 40 of individual interconnected traces 42 of the device 60 can be simultaneously patterned on the elastomeric layer from the same conductive layer. With the exception of the electrodes 44 and connecting means 64, the device 60 and wireless unit 62 are shown in FIG. 14 as encapsulated with a suitable encapsulation material 66 to mechanically and electrically isolate their electronic components from the skin and environment as well as promote adhesion to the skin.

While the invention has been described in terms of specific or particular embodiments and investigations, it should be apparent that alternatives could be adopted by one skilled in the art. For example, the nanocomposite elastomer structures, composite elastomer structures, and their components could differ in appearance and construction from the embodiments described herein and shown in the drawings, functions of certain components of the nanocomposite elastomer structures could be performed by components of different construction but capable of a similar (though not necessarily equivalent) function, and appropriate materials could be substituted for those noted. In addition, the nanocomposite and composite elastomer structures could be used in various devices and systems comprising additional components. Accordingly, it should be understood that the invention is not necessarily limited to any embodiment described herein or illustrated in the drawings. It should also be understood that the phraseology and terminology employed above are for the purpose of describing the disclosed embodiments and investigations, and do not necessarily serve as limitations to the scope of the invention. Therefore, the scope of the invention is to be limited only by the following claims.

The invention claimed is:

1. A skin-mountable electronic device adapted for measuring muscle activity in a human body, the skin-mountable electronic device comprising:
   a flexible structure comprising an elastomeric layer and an electrically-conductive layer that overlies and directly contacts an underlying portion of the elastomeric layer, wherein each of the elastomeric layer and the electrically-conductive layer forms a deformable honeycomb pattern of individual traces and connections therebetween, each of the individual traces and the connections therebetween comprising a portion of the elastomeric layer, and at least some and fewer than all of the individual interconnected traces and the connections therebetween comprising portions of the electrically-conductive layer, the portions of the electrically-conductive layer defining multiple different conductive paths that include at least first and second conductive paths that are not electrically connected to each other within the flexible structure, the first conductive path comprising the portions of the electrically-conductive layer of a first plurality of the individual traces that are electrically connected to each other in electrical series, the second conductive path comprising the portions of the electrically-conductive layer of a second plurality of the individual traces that are electrically connected to each other in electrical series;
   functional electrodes located within the honeycomb pattern, the functional electrodes comprising at least a first functional electrode that is electrically connected to the first conductive path and a second functional electrode that is electrically connected to the second conductive path; and
   an electrical connector for electrically connecting an electronic unit to the functional electrodes, the electrical connector being electrically connected to at least the first and second functional electrodes through, respectively, the first and second conductive paths.

2. The skin-mountable electronic device of claim 1, wherein the functional electrodes are located within openings within the honeycomb pattern.

3. The skin-mountable electronic device of claim 2, wherein the honeycomb pattern contains a region that is free of the individual traces for receiving a sensor.

4. The skin-mountable electronic device of claim 1, wherein the electrically-conductive layer is formed by a patterned mesh of nanowires that comprises a layer of a network of randomly oriented metallic nanowires.

* * * * *